(12) United States Patent
Qi et al.

(10) Patent No.: US 8,507,462 B2
(45) Date of Patent: Aug. 13, 2013

(54) COMPOSITIONS AND USES THEREOF

(75) Inventors: Xin Qi, Glasgow (GB); Richard Tester, Glasgow (GB)

(73) Assignee: Glycologic Limited, Glasgow Caledonian University, Glasgow (GB)

( * ) Notice: Subject to any disclaimer, the term of this patent is extended or adjusted under 35 U.S.C. 154(b) by 1063 days.

(21) Appl. No.: 10/578,551

(22) PCT Filed: Nov. 8, 2004

(86) PCT No.: PCT/GB2004/004682
§ 371 (c)(1),
(2), (4) Date: Jun. 29, 2006

(87) PCT Pub. No.: WO2005/044284
PCT Pub. Date: May 19, 2005

(65) Prior Publication Data
US 2007/0077277 A1    Apr. 5, 2007

(30) Foreign Application Priority Data
Nov. 6, 2003  (GB) .................................. 0325942.1

(51) Int. Cl.
*A61K 31/715* (2006.01)

(52) U.S. Cl.
USPC ............. 514/60; 424/439; 424/441; 426/808; 426/661; 426/549; 426/567; 514/54; 514/866

(58) Field of Classification Search
USPC ................................................ 426/549, 567
See application file for complete search history.

(56) References Cited

U.S. PATENT DOCUMENTS

| 4,418,090 | A | * | 11/1983 | Bohrmann et al. ........... 426/578 |
| 5,576,048 | A | | 11/1996 | Hauber et al. |
| 5,605,893 | A | | 2/1997 | Kaufman et al. |
| 2001/0019734 | A1 | * | 9/2001 | Gilbertson et al. ........... 426/549 |
| 2003/0045504 | A1 | | 3/2003 | Brown et al. |
| 2003/0054501 | A1 | | 3/2003 | Schmiedel et al. |

FOREIGN PATENT DOCUMENTS

| GB | 1 306 384 A | 2/1973 |
| WO | WO 02/34271 A | 5/2002 |

OTHER PUBLICATIONS

Metabolic Energy, 1988, Stryer, Lubert, Biochemistry, Third Edition, p. 342.*
Lindley et al., Surgery of persistent hyperinsulinaemic hypoglycaemia, 2003, Seminars in Neonatology, vol. 8, pp. 259-265.*
Anderson et al., Digestibility and Pasting Properties of Rice Starch Heat-Moisture Treated at the Melting Temperature (™), Starch, vol. 54, 2002, pp. 401-409.*
Reiser, S., "Simple and complex carbohydrates", *Livingston, G.E.*, USA (1990).
Behall et al., "Effect of Starch Structure on Glucose and Insulin Responses in Adults", *American Journal of Clinical Nutrition*:47:428-432 (1988).

* cited by examiner

*Primary Examiner* — Lezah Roberts
*Assistant Examiner* — Nannette Holloman
(74) *Attorney, Agent, or Firm* — Janet Sleath; Speckman Law Group PLLC

(57) ABSTRACT

Methods of controlling serum glucose levels in an individual are described, the methods including the step of administering to said individual a therapeutic food composition comprising a waxy and/or hydrothermally treated starch. The method may be used to treat or prevent hypoglycaemia in patients susceptible to hypoglycaemic episodes, for example patients with glycogen storage disease, diabetes or liver disease. The method may also be used in sports nutrition. Also described are compositions for use in the methods.

18 Claims, 14 Drawing Sheets

Glycogen Synthesis (Glucose Storage)

Branched glucan ($\alpha$-(1-4) and ($\alpha$-(1-6) bonds) formed from glucose and stored as spherical granules (10-40 nm in diameter)

- Promoted by insulin a. *Linear glycogen chain synthesis – formation of G6P from glucose*

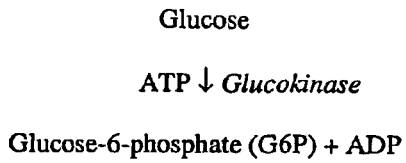

b. *Linear glycogen chain synthesis – formation of G1P from G6P*

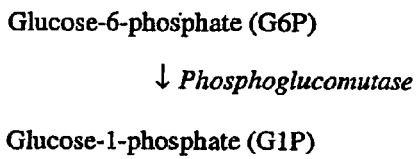

c. *Linear glycogen chain synthesis – formation of UDP*

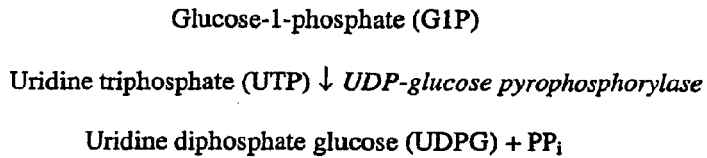

d. *Linear glycogen chain synthesis – formation of linear chains*

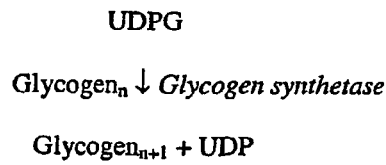

e. *Introduction of $\alpha$-(1-6) glycogen branches*

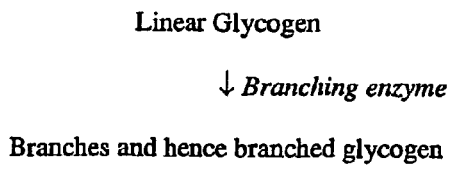

Figure 1 (part 1). Glucose metabolism

Glycogen Hydrolysis and Glucose Formation

- Promoted by adrenaline (especially muscle)
- Promoted by glucagon (especially liver)

*f. Linear glycogen chain hydrolysis*

$$\text{Linear } \alpha\text{-(1-4) Glycogen Residues}$$

$$+P_i \downarrow \textit{Glycogen phosphorylase}$$

$$\text{Glycogen}_{n-1} + \text{Glucose -1-phosphate (G1P)}$$
[glucose cleaved from non-reducing end]

*g. Conversion of G1P to G6P*

$$\text{Glucose-1-phosphate (G1P)}$$

$$\downarrow \textit{Phosphoglucomutase}$$

$$\text{Glucose-6-phosphate (G6P)}$$

*h. Conversion of G6P to glucose*

$$\text{Glucose-6-phosphate (G6P)}$$

$$\downarrow \textit{Glucose-6-phosphatase}$$

$$\text{Glucose} + P_i$$

*i. Glycogen branch point hydrolysis*

$$\text{Branched } \alpha\text{-(1-6) Glycogen Residues}$$

$$\downarrow \textit{Transferase/ debranching enzyme}$$

Linear Glycogen from transferase activity from α-(1-6) bond
+
Glucose from branch residue (debranching/glucosidase activity)

*Note: Blood glucose is maintained at about ~4.5mmol $l^{-1}$ in man.*

Figure 1 (part 2). Glucose metabolism

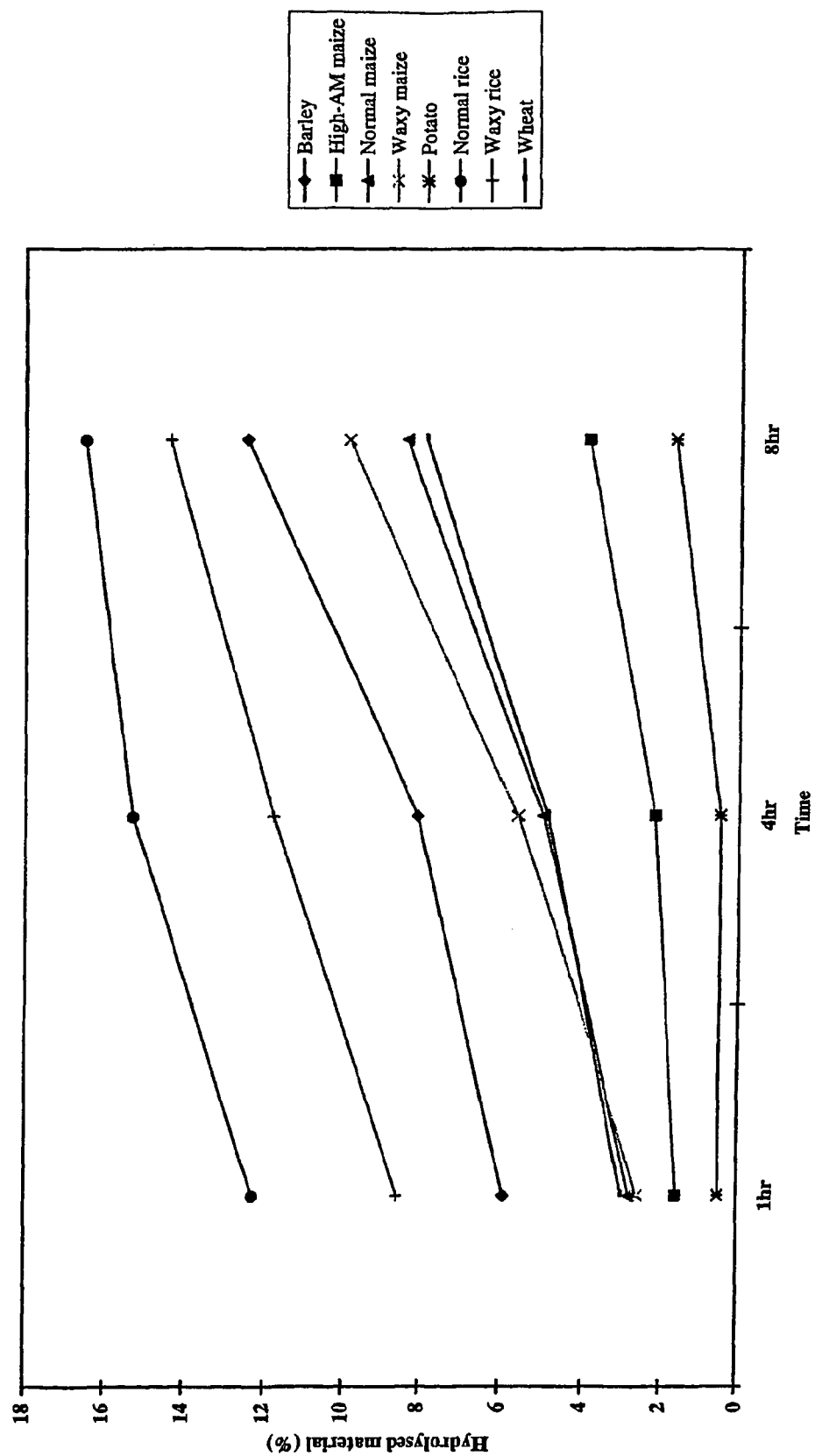
Figure 2: Comparison of the hydrolysis profile of native starches using the Karkalas et al (1992) procedure.

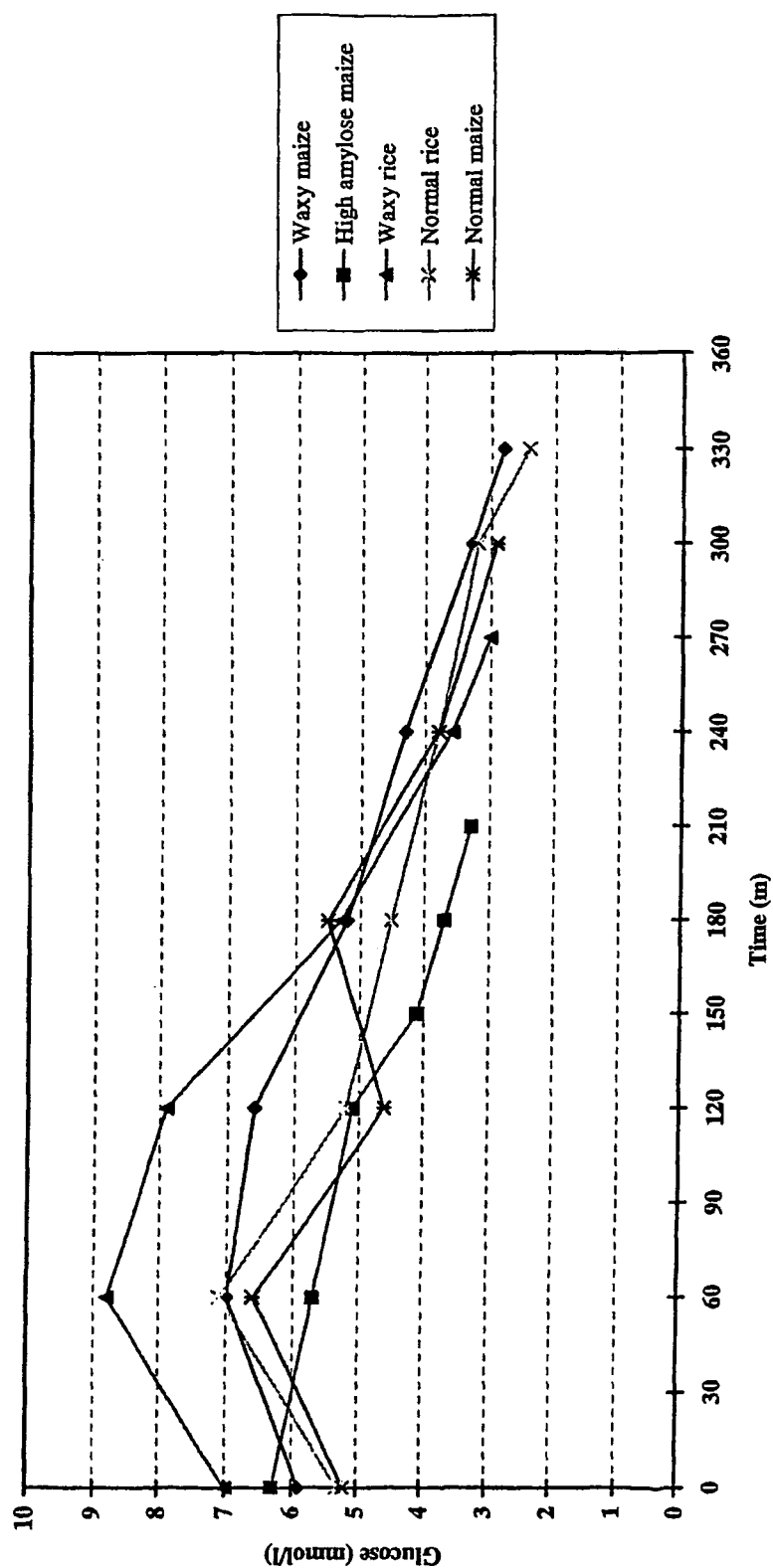
Figure 3: Blood glucose level after consumption of native starches

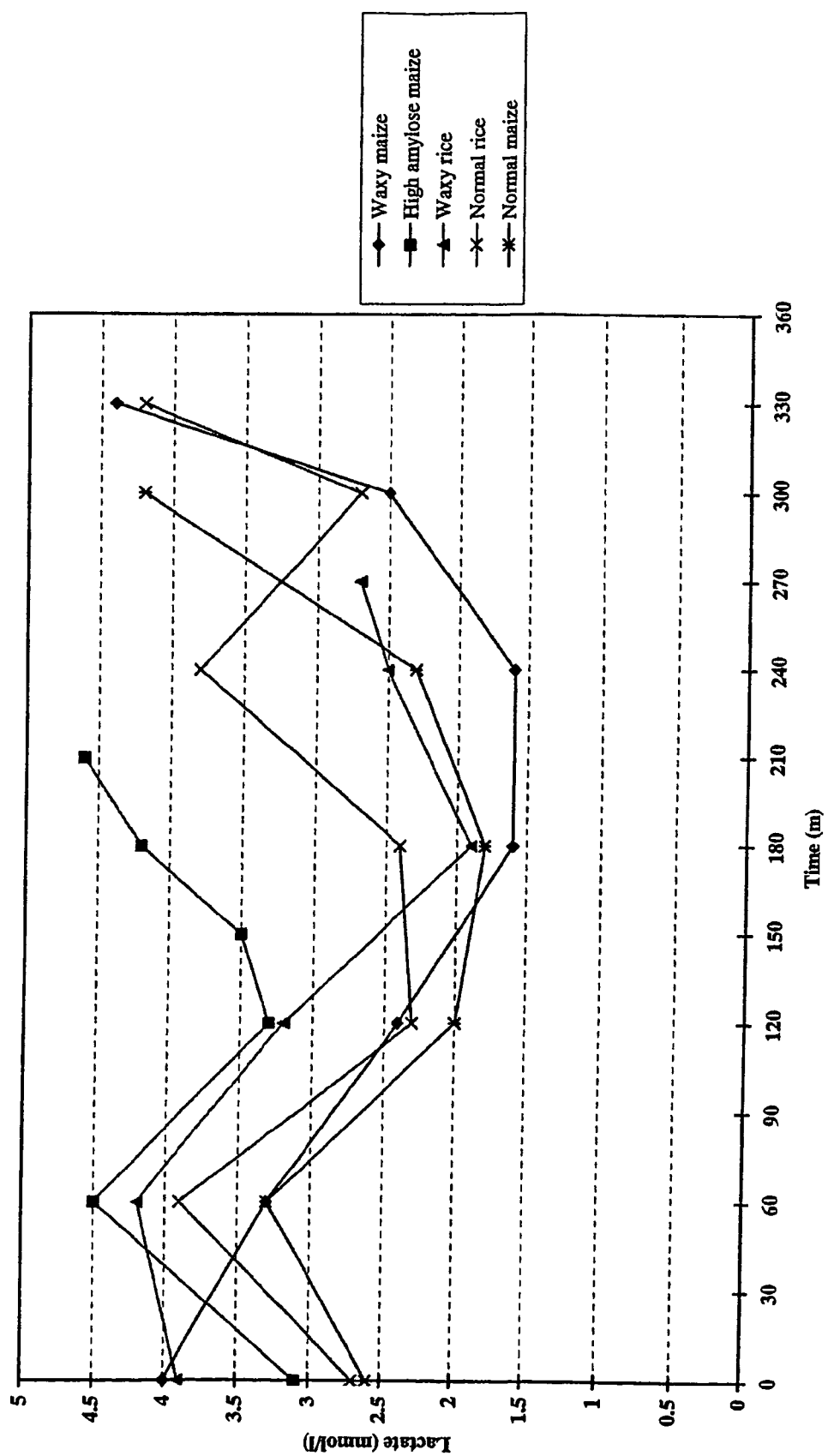
Figure 4: Comparison of the blood lactate level after consumption of native starches

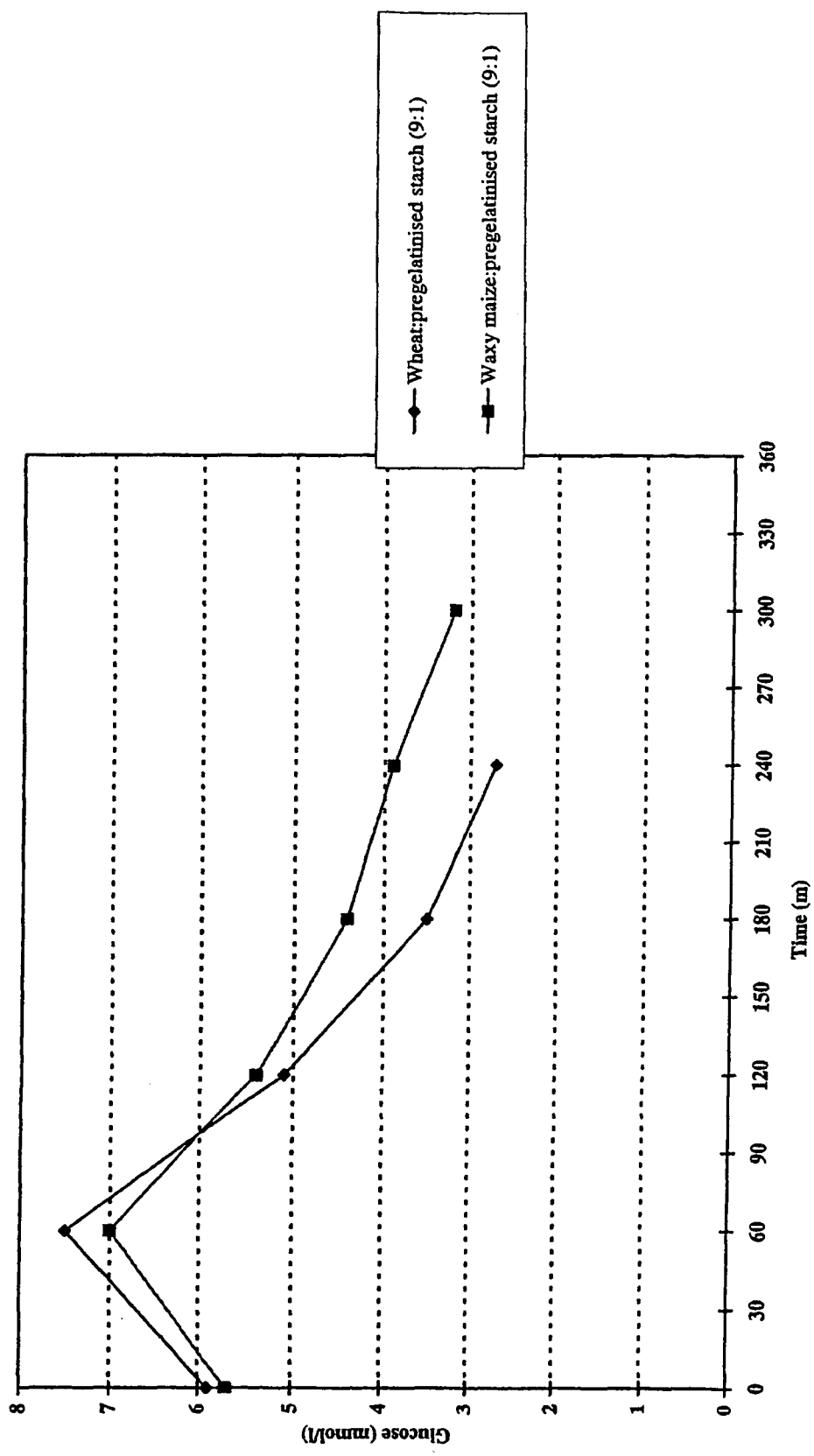
Figure 5: Comparison of blood glucose after consumption of two native starches (wheat and waxy maize) with added pregelatinised (maize) starch.

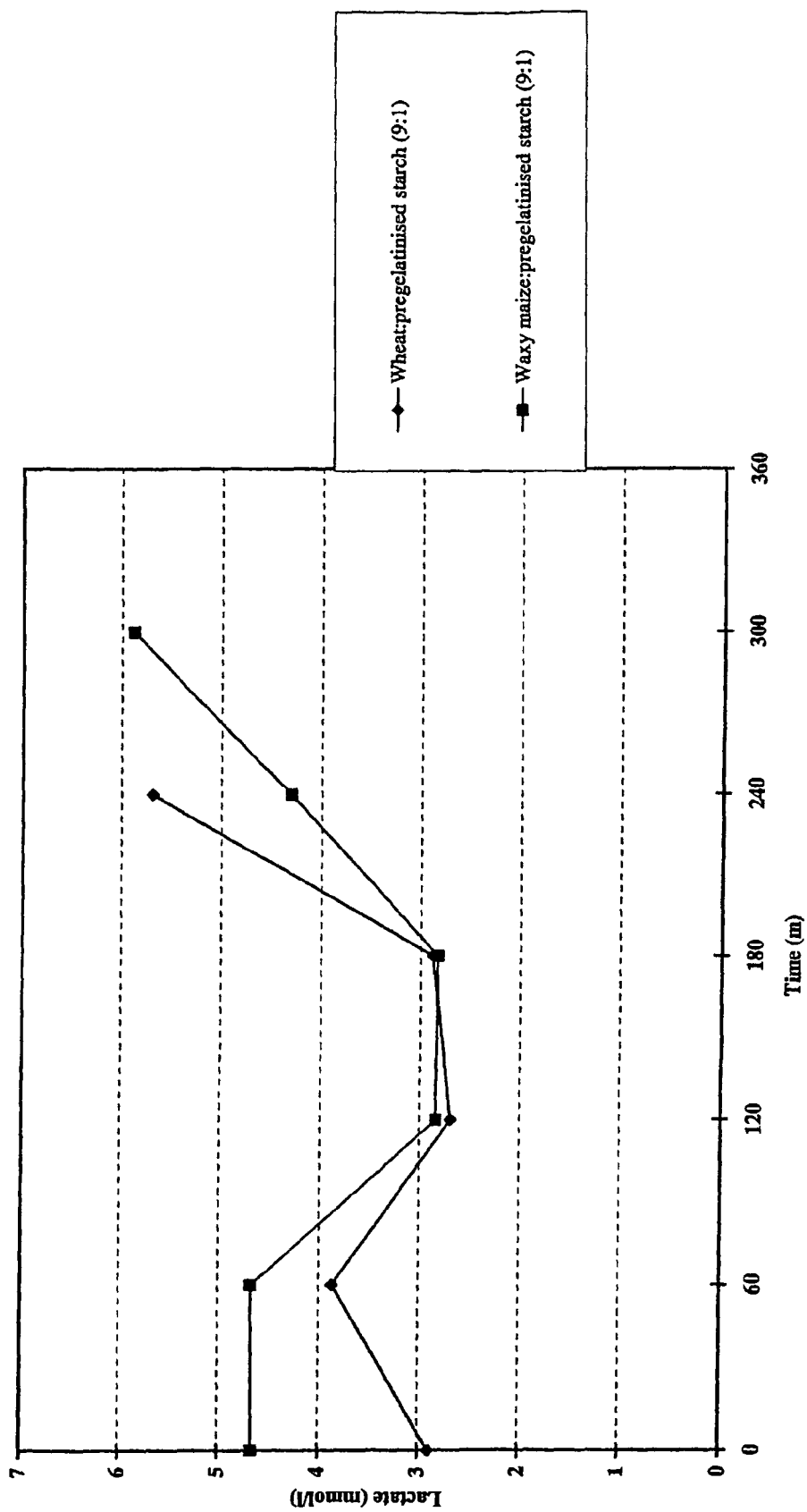
Figure 6: Comparison of the blood lactate level after consumption of two native starches (wheat and waxy maize) with added pregelatinised (maize) starch

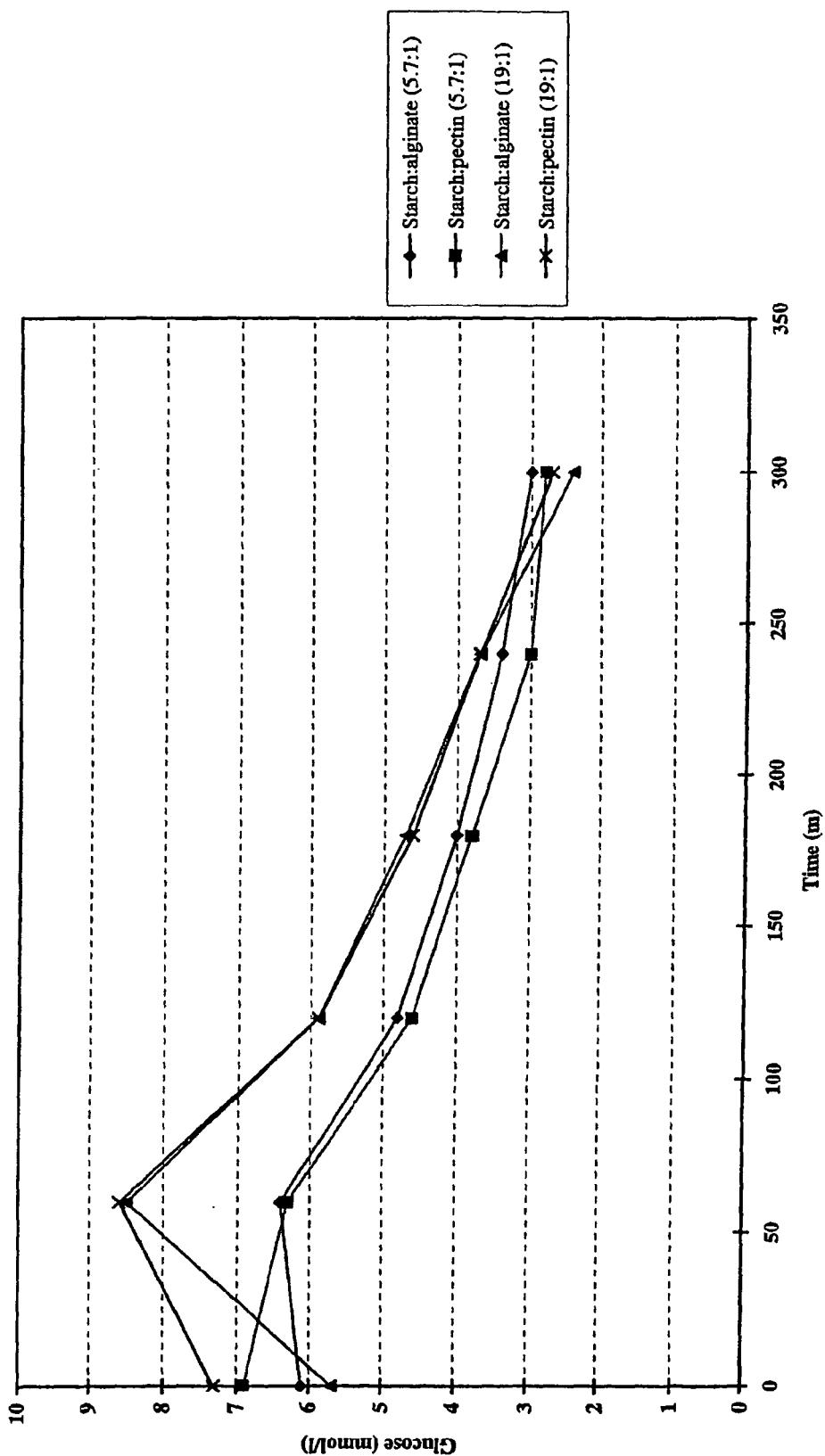
Figure 7: Comparison of blood glucose after consumption starch (native waxy maize and soluble) encapsulated with pectin or alginate.

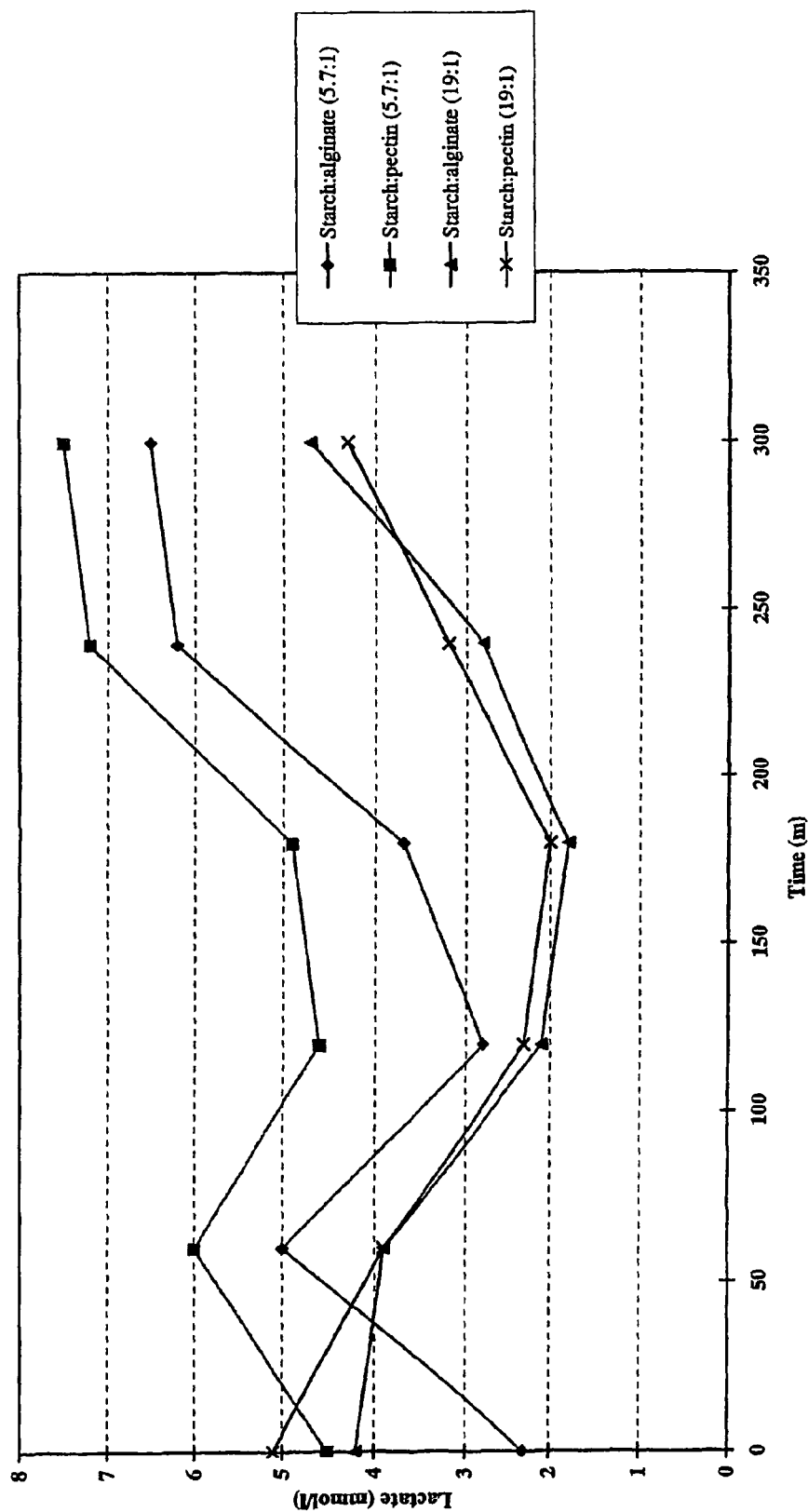
Figure 8: Comparison of blood lactate after consumption of starch (native waxy maize and soluble) encapsulated with pectin or alginate

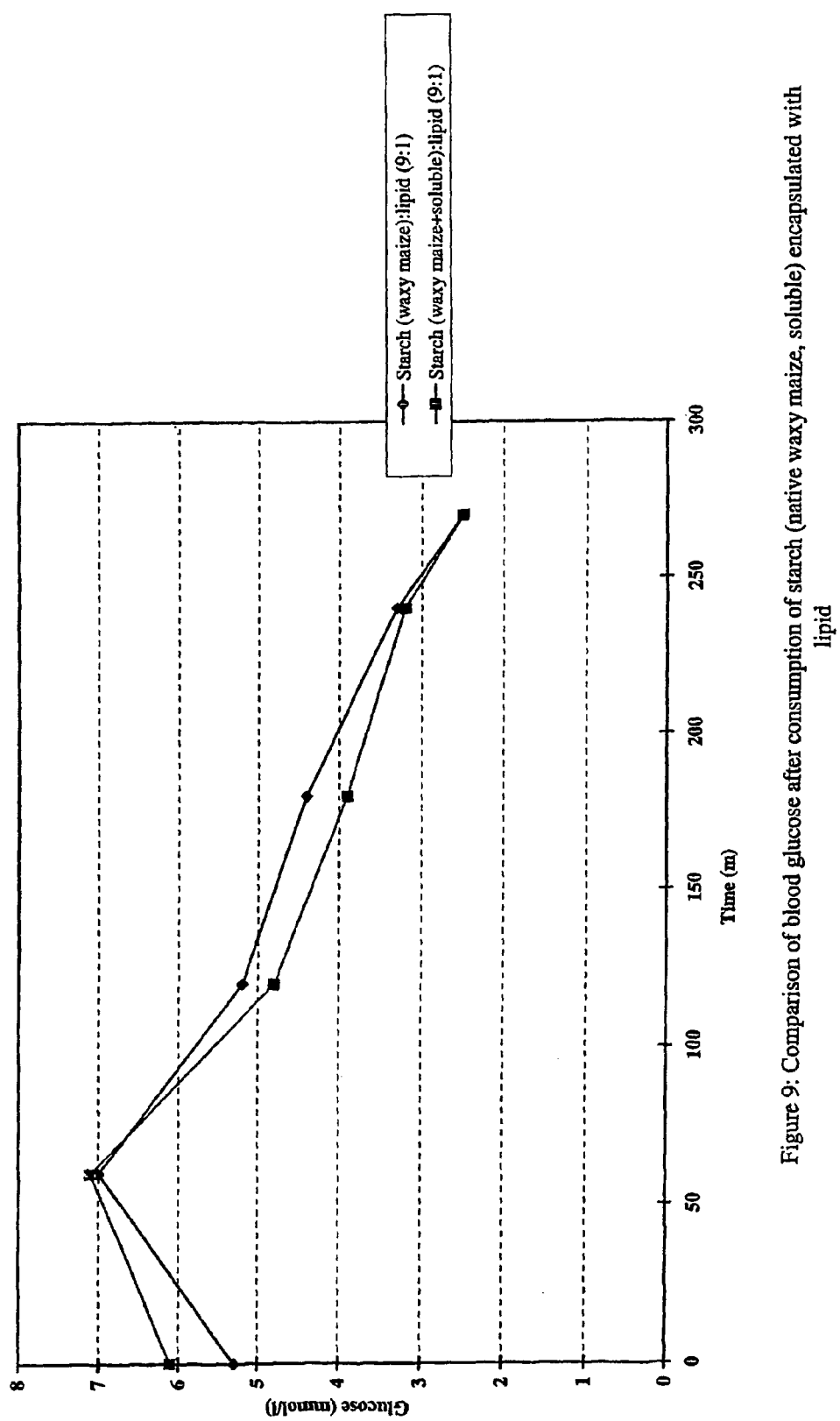
Figure 9: Comparison of blood glucose after consumption of starch (native waxy maize, soluble) encapsulated with lipid

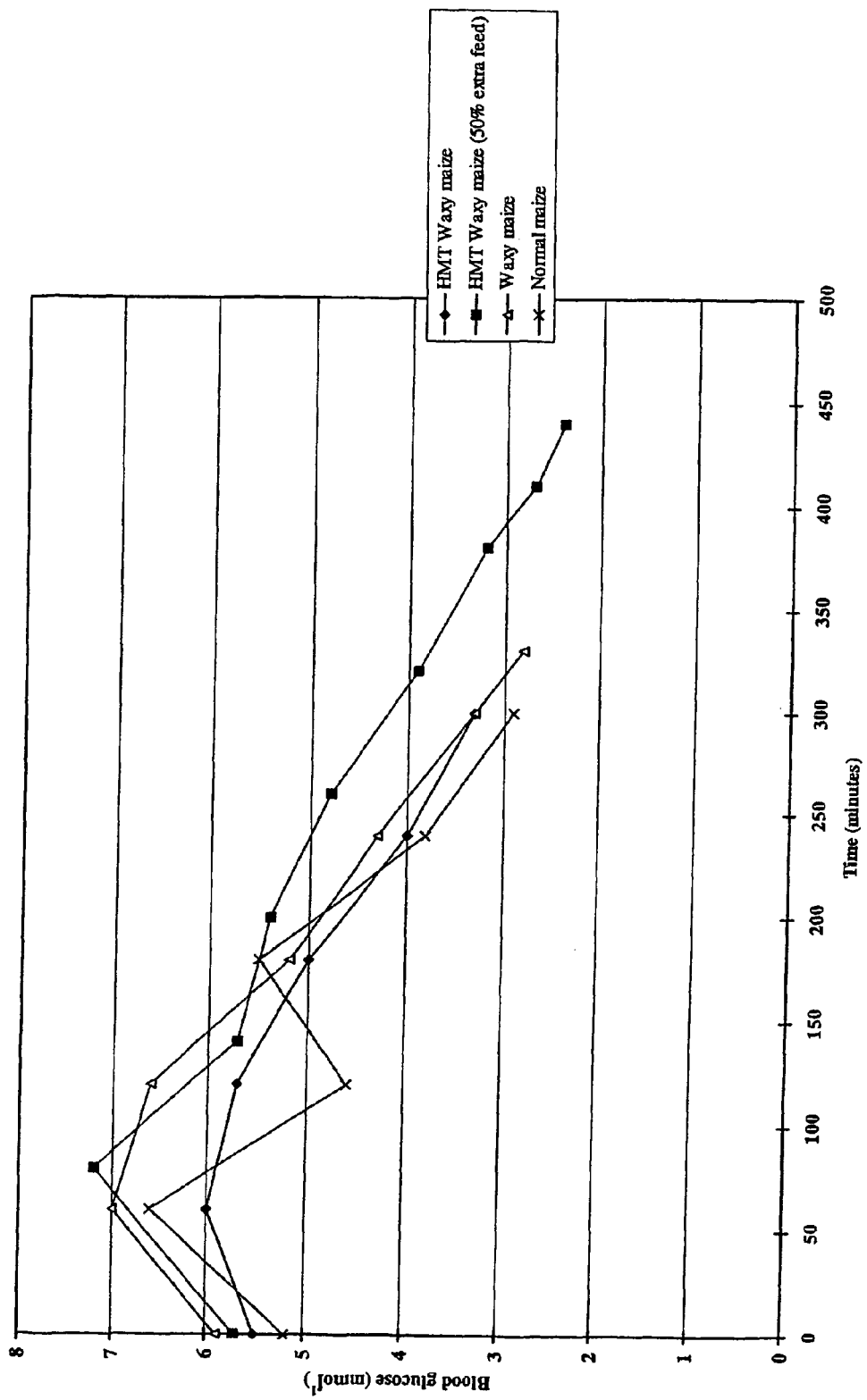
Figure 10: Comparison of blood glucose after consumption of heat-moisture treated waxy maize starch, waxy maize and normal maize starch.

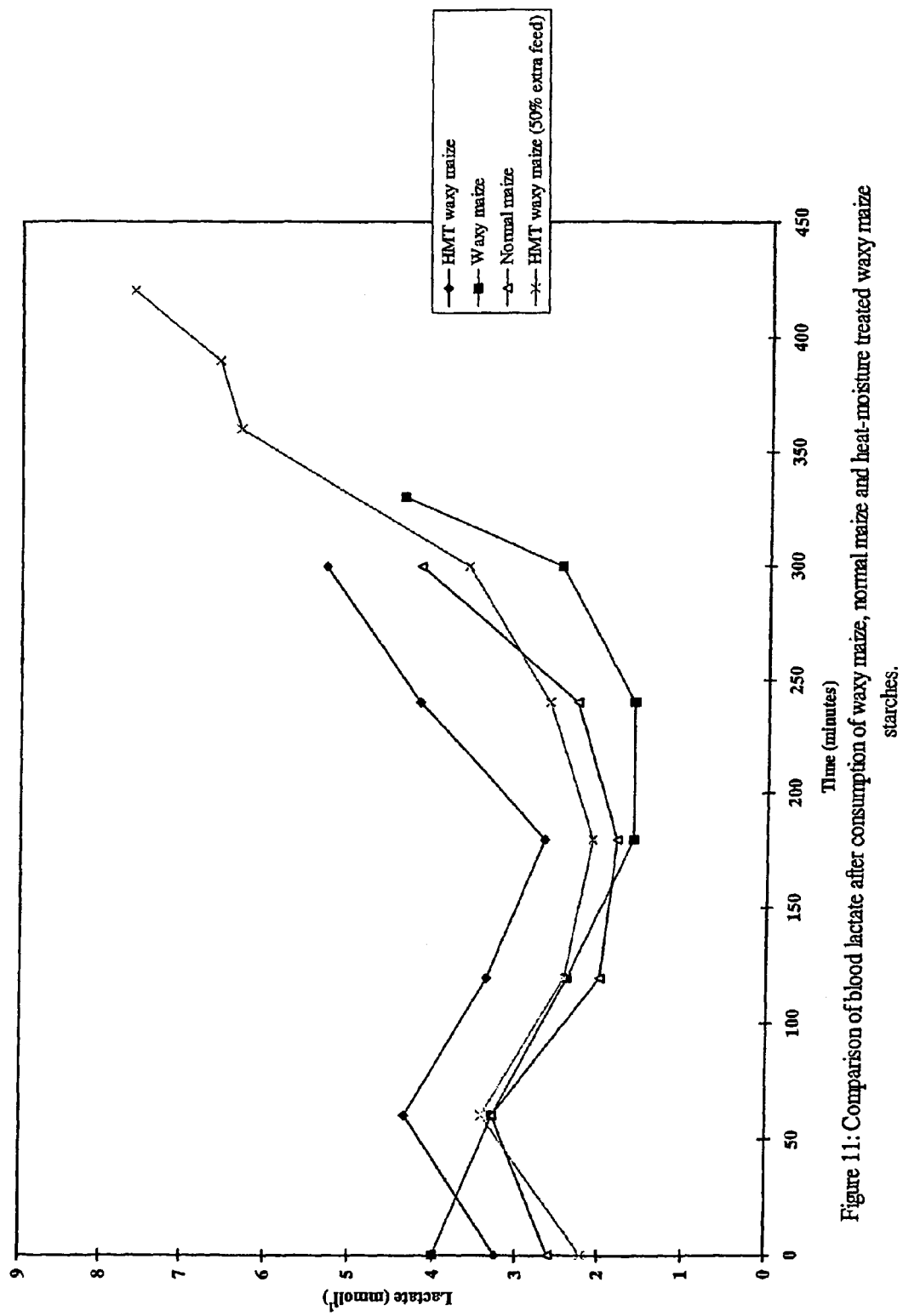
Figure 11: Comparison of blood lactate after consumption of waxy maize, normal maize and heat-moisture treated waxy maize starches.

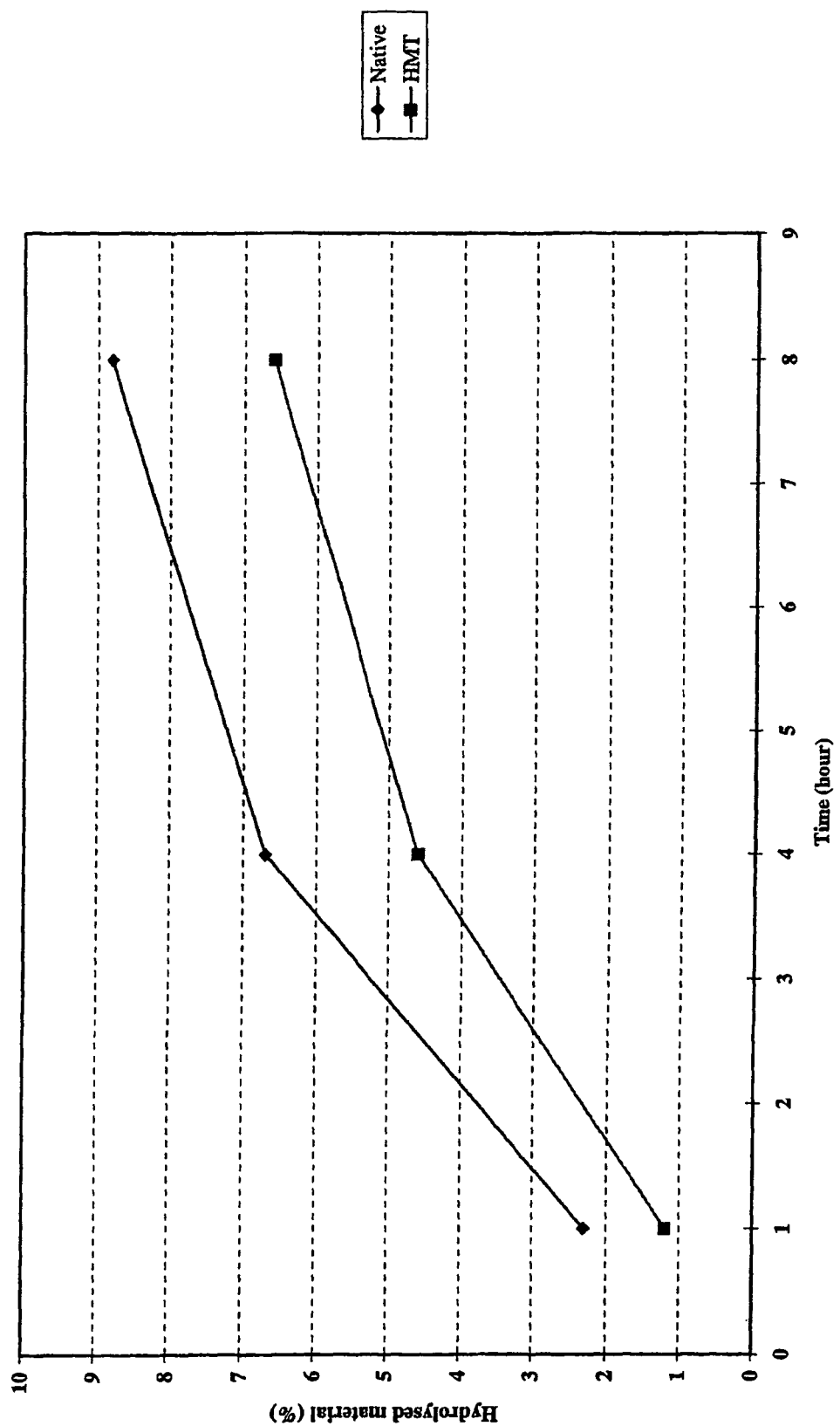
Figure 12: Comparison of digestibility of native and heat-moisture treated waxy maize starches

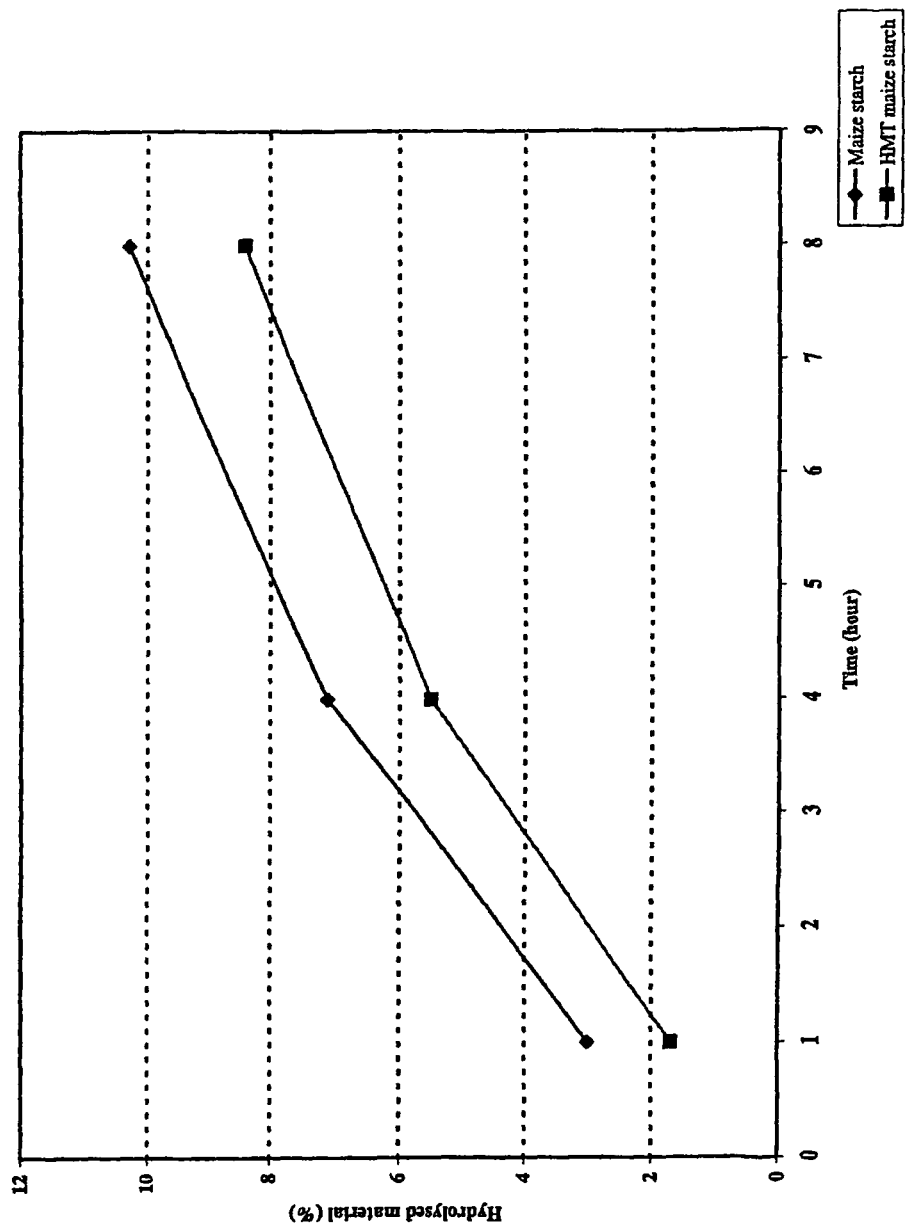
Figure 13: Comparison of digestibility of native and heat-moisture treated maize starches

COMPOSITIONS AND USES THEREOF

FIELD OF THE INVENTION

The present invention relates to methods of controlling serum glucose levels in mammals. In particular it relates to methods for the prevention of severe fluctuations in glucose levels and the use of these methods in the treatment of diseases characterised by hypoglycaemia, such as glycogen storage disease (GSD), clinical conditions where a slow release of energy in the form of glucose may be required (e.g. diabetes) and for sports and fitness type products where a slow release of energy is desirable.

BACKGROUND TO THE INVENTION

The release of energy from foods and food products is a complex process. It depends on the composition, structure, extent of modification and volume of the food. Apart from this, it is also variable between individuals and reflects many different factors which probably include a combination of age, level of fitness, rate of gastric emptying and peristalsis, sex, size, state of health etc. Energy may be derived from different food sources, for example, carbohydrates, lipids and proteins, alcohol etc. In many animals, including man, energy is stored as fat (adipose tissue) and provides a reserve when food is limiting. There is a more readily available form of energy, however, where a glucose polymer (glycogen) is stored in muscles and the liver and can be rapidly mobilised when required. The formation and storage of glycogen is a synchronised enzymatic process which is controlled in part by insulin which promotes the formation of glycogen from the glucose precursors (FIG. 1). Glucose deposition and glycogen catabolism is co-ordinated in man to maintain blood glucose at ~4.5 mmol l$^{-1}$.

Glycogen Storage Disease

In the normal human, the anabolism and catabolism of glycogen is normally co-ordinated and regulated. The deposition of glycogen is promoted by insulin whilst the hydrolysis of glycogen and conversion to glucose is promoted by adrenaline (especially muscle) and glucagons (especially liver).

In glycogen storage disease (GSD) there is an inherited defect with respect to the deposition or hydrolysis of glycogen (http<<colon>>//www<<dot>>agsd<<dot>>org<<dot>>uk/home/information<<dot>>asp>; http<<colon>>//agsdus<<dot>>org/body_whatis_1<<dot>>html) and consequently the concentration of blood glucose. FIG. 1 outlines the principles of glycogen metabolism.

The most common types of glycogen storage disease are:

In Type I (Von Gierke Disease) individuals suffer from a lack of glucose-6-phosphatase activity ('h' in FIG. 1) and hence cannot generate glucose from glycogen. Consequently they need to be tube fed to maintain blood glucose.

In Type II (Pompe's Disease) individuals suffer from a lack of α-glucosidase activity ('i' in FIG. 1). Infants often die of this form very young.

In Type III (Cori's Disease) individuals suffer from a lack of debranching enzyme activity ('i' in FIG. 1). Treatment usually consists of a high protein diet.

In Type IV (Anderson's Disease) individuals suffer from a lack of branching enzyme activity ('e' in FIG. 1). Liver transplantation is the only viable therapy.

In Type V (McArdle's Disease) individuals suffer from a lack of muscle phosphorylase activity ('f' in FIG. 1). Extensive exercise should be avoided.

In Type VI (Her's Disease) individuals suffer from a lack of liver phosphorylase activity ('f' in FIG. 1). There is a male X-chromosome link.

In Type VII (Tarui's Disease) individuals suffer from a lack of muscle phosphofructokinase activity. Extensive exercise should be avoided.

In Type IX individuals suffer from a lack of liver phosphorylase activity ('f' in FIG. 1). There is a male X-chromosome link and it is comparable to type VI.

Low blood glucose can be treated by the slow administration of glucose (oral or intravenous), or from starch hydrolysates (e.g. maltose, dextrins etc.) or from native starch where glucose is liberated as a consequence of digestion. In practice 'corn-starch', which is normal maize starch, is used to treat glycogen storage disease (especially during sleep) due to availability and to lack of a superior alternative in terms of digestive response. The starch must be slowly digested and not converted to glucose rapidly or excreted with little hydrolysis. In other clinical conditions (such as diabetes mellitus) there is also the need to supply glucose slowly and from a non-sugar based matrix (e.g. cakes, biscuits, sweets etc.). This can, therefore, also be achieved by starch (hydrolysis in the gut) and is important for night time regimes where glucose is essential in the blood but within a controlled form.

The advantages and disadvantages of feeding glucose, maltodextrins or maize starch for clinical nutrition with a perceived optimal substrate are defined in Table 1.

TABLE 1

Release profile of glucose based substrates in the gut of man with perceived optimised product in this respect

| Entry to body | Glucose | Malto-dextrin | Normal maize ('corn') starch | |
|---|---|---|---|---|
| Intravenous | Used extensively in medicine. Would need to be pumped constantly for GSD and diabetes clinical maintenance. | Too high molecular weight | Inappropriate in view of size, composition and structure | Appropriate in view of size, composition and structure |
| Oral - small intestine | Rapidly absorbed (1.5 hours) | Rapidly absorbed (1.5 hours) | Glucose released within 4 hours | Glucose released over 7.5 hours (to provide overnight release) |
| Oral - large intestine | Not applicable | Not applicable | Possibly mostly digested with small amount of fermentable substrate | Minimal fermentable substrate to avoid loss of energy and fermentation |

Slow Release of Energy

Apart for the clinical conditions described above, athletes require sustained release of energy. There are many products on the market which release energy based on sugars or maltodextrins. These include products presented in Table 2. However, sugars and dextrins are absorbed very rapidly and these products must be consumed regularly to maintain the required body loading of the energy.

TABLE 2

Energy based products currently found on the market.

| Product | Carbohydrate, % of product | Carbohydrates used as energy source |
|---|---|---|
| Accelerade | 7.75 | Fructose, maltodextrin and sucrose |
| Allsport | 9.00 | High fructose syrup |
| Cytomax | 6.00 | High fructose syrup and maltodextrin |
| Enervit G | 7.60 | Fructose, glucose, maltodextrin and sucrose |
| Extran thirstquencher | 5.00 | Fructose and maltodextrin |
| G Push | 7.50 | Fructose, galactose and maltodextrin |
| Gatorade | 6.00 | Fructose, glucose and sucrose |
| GU20 | 5.70 | Fructose and maltodextrin |
| Powerade | 8.00 | High fructose syrup and glucose polymers [sic] |
| Revenge Sport | 7.00 | Fructose, glucose and maltodextrin |

(adapted from www<<dot>>accelerade<<dot>>com/accelerade-comparison-results<<dot>>asp)

Slow Energy Release Nutritional Formulations

As mentioned above, slow release products for sports nutrition tend to be pouched relying on glucose or maltodextrin to supply the energy. These actually are absorbed quickly as they are either readily absorbed (e.g. glucose) or converted to glucose relatively rapidly (e.g. maltodextrins, probably within 60 minutes maximum).

On the other hand, glycogen storage disease (certain treatable forms, see above) management requires that patients receive a slow release of glucose, especially, for example, overnight. Native starch is provided for this purpose where: the initial liberation phase of glucose is not too rapid (see figures below); glucose is released at as constant a rate as possible which must not be too slow or too fast and; the production of lactate (anaerobic respiration) is minimised. Certain starches are to be avoided as they exhibit only limited hydrolysis in the native form (e.g. potato).

Hence, the extent and rate of starch digestion are important parameters with respect to glucose release from the ingested α-glucan. Regulation in terms of these parameters reflect the state of the starch and the rate at which the energy source travels through the gut. A balance in terms of energy release is required which can be controlled by the energy source and the transit time.

Osmolality is also an important feature with respect to carbohydrate usage. Sugar solutions exert a high osmotic pressure compared to polysaccharides due to the number of moles in solution.

The viscosity of the consumed material will also affect the capacity for it to be hydrolysed and to permit associated compounds to come into contact with the mucosal surface. This is a very important issue with respect to product development regarding potential energy sources.

Glycaemic Index (GI) is also an important determinant of energy availability from foods and more especially α-glucans. In this context, white bread has a GI of 1 which is the same as pure glucose and represents one hundred percent availability of the α-glucan fraction (or 1 on a scale from 0 to 1).

Gastric Emptying

As mentioned above, the rate and extent of gastric emptying will in part regulate the transit time of food materials through the gut. It is established that high volumes—low energy promote gastric emptying whereas low volumes—high energy restrict gastric emptying. Lipids and proteins are valuable aids with respect to restricting emptying of the stomach.

Glycogen storage disease and diabetes are classically managed by feeding 'cornstarch' which is normal maize starch (Kaufman, 2002). Sometimes, proportions of carbohydrates are utilised which provide rapid (e.g. sugar), medium (e.g. gelatinised starch) and slow ('cornstarch') digestion and hence glucose appearance in the blood (Wilbert, 1998). Sugar combinations with or without maltodextrins or 'glucose polymers' are often employed in 'energy drinks' (including rehydration drinks) and often with other components like salts, protein, fatty acids, glycerol, minerals, flavouring etc. (Gawen, 1981; Tauder et al, 1986; Burling et al, 1989; Gordeladze, 1997; Paul and Ashmead, 1993 and 1994; Vinci et al, 1993; Fischer et al, 1994; Simone, 1995; Gordeladze, 1997; King, 1998; Kurppa, 1998; Cooper et al, 2001; Portman, 2002). The maltodextrins/glucose polymers are used to slow energy availability (compared to sugars) and exert less osmotic pressure.

Brynolf et al (1999) describe the production of an acid modified starch with a molecular weight of 15,000 to 10,000,000 produced by classical acid hydrolysis of starch to be used as an energy source prior to physical activity. Lapré et al (1996) have discussed the option of coating food with non-starch polysaccharides (cation gelling) to reduce the glycaemic response of carbohydrate containing foods.

However, although currently available starch preparations used in the treatment of conditions such as GSD have prolonged glucose release profiles compared to glucose and maltodextrin based products, the time period over which the products enable serum glucose levels to be maintained within an acceptable range is relatively short. Thus, at present, using conventional oral preparations, patients susceptible to hypoglycaemic episodes generally must ingest such glucose sources at intervals of no longer than 4 hours. Although this may be acceptable during daytime, the need for repeated feeding is very inconvenient at nighttime. The patient thus must either awake or be wakened overnight to feed or, alternatively, sleep with a nasogastric tube in place to provide a constant source of glucose.

Accordingly, there is a great need for alternative means of maintaining serum glucose levels within safe ranges over a longer period of time than that afforded by the conventional treatments.

SUMMARY OF THE INVENTION

The present inventors, after considerable work, have surprisingly discovered that semi-crystalline waxy starches afford significantly prolonged glucose release in the human GI tract compared to normal or high amylose semi-crystalline starches as conventionally used in preparations for slow energy release.

Accordingly, in a first aspect, the present invention provides a method of controlling serum glucose levels in an individual said method including the step of administering to said individual a therapeutic food composition comprising a waxy starch.

In a second aspect, the invention provides a method of treating or preventing hypoglycaemia in an individual said method including the step of administering to said individual a therapeutic food composition comprising a waxy starch.

According to a third aspect, the invention provides a method of treating an individual susceptible to hypoglycaemic episodes, said method including the step of administering to said individual a therapeutic food composition comprising a waxy starch.

In one preferred embodiment, said treatment is treatment to prevent or decrease night-time hypoglycaemic episode(s).

As described herein, the inventors have found that waxy starches provide prolonged glucose release when ingested.

Moreover, as well as discovering that such semi-crystalline starches provide advantageous slow glucose release, the inventors have unexpectedly found that the time period over which glucose may be released from starches and thus the time period over which serum glucose levels may be maintained in patients without the need for further doses of food compositions can be markedly increased by hydrothermal treatment of starches for use in the invention. Indeed, as demonstrated in the Examples below, the time period over which serum glucose levels may be maintained in patients without the need for further doses of food compositions may be prolonged by use of such hydrothermally treated starches (for example heat moisture treated starches) to more than six hours, indeed typically more than 7 hours. Thus, the use of such starches (or indeed other hydrothermally treated starches) in the methods of the invention enables a patient susceptible to night-time hypoglycaemic episodes to sleep for a substantially normal duration i.e. more than 6 hours, preferably more than 7 hours, without the need for nasogastric feeding or further food doses throughout the night.

Accordingly, in preferred embodiments of the invention, the starch is hydrothermally treated (HTT) waxy starch. Preferably said hydrothermally treated waxy starch is heat-moisture treated (HMT) waxy starch.

However, as well as finding that hydrothermal treatment has very advantageous effects on waxy starches, the inventors have also shown that hydrothermal treatment also improves and prolongs the glucose release profile of non-waxy starches.

Accordingly, in a fourth independent aspect of the present invention, there is provided a method of controlling serum glucose levels in an individual said method including the step of administering to said individual a therapeutic food composition comprising a hydrothermally treated starch.

In a fifth aspect, the invention provides a method of treating or preventing hypoglycaemia in an individual said method including the step of administering to said individual a therapeutic food composition comprising a hydrothermally treated starch.

According to a sixth aspect, the invention provides a method of treating an individual susceptible to hypoglycaemic episodes to prevent or decrease hypoglycaemic episode(s), said method including the step of administering to said individual a therapeutic food composition comprising hydrothermally treated starch.

In one preferred embodiment, said treatment is treatment to prevent or decrease night-time hypoglycaemic episode(s).

In the fourth, fifth and sixth aspects of the invention, any suitable hydrothermally treated starch may be used. Said hydrothermally treated starch may be starch which has been heat moisture treated or starch which has been subjected to annealing treatment. In preferred embodiments the hydrothermally treated starch is heat moisture treated starch.

In preferred embodiments of the invention, starch of and for use in the invention is a "waxy starch".

Waxy starches for use in any aspect of the present invention may be any starch having an amylopectin content of at least 70%, preferably at least 80%, more preferably at least 85%, even more preferably at least 90%, yet more preferably at least 95%, most preferably at least 98% amylopectin. Such waxy starches may be cereal or non-cereal waxy starches.

Preferably, said waxy starch is a waxy cereal starch, for example waxy maize starch.

Preferably, the starch of and for use in the invention should have a granular size in the range 10 to 35 μm, more preferably in the range 15 to 30 μm.

Preferably the starch used in the invention enables a blood glucose concentration of greater than 3.0 mmol l$^{-1}$ at 300 min post administration.

In preferred embodiments, the therapeutic food composition is such that it, in use, its administration results in a maximum blood glucose concentration of no greater than 9 mmol l$^{-1}$. In a further embodiment, in use, administration of the therapeutic food composition results in a maximum blood glucose concentration of no greater than 8 mmol l$^{-1}$.

In particularly preferred embodiments, the starch, in use, enables a blood glucose concentration of greater than 3.0 mmol l$^{-1}$ at 300 min post administration, but does not cause a peak in blood glucose concentration of any greater than 9.0 mmol l$^{-1}$, for example not greater than 8.0 mmol l$^{-1}$ References to blood glucose concentration relate to a typical adult human of normal weight, for example 72 kg.

Preferably therapeutic food compositions of and for use in the method of the present invention comprise per unit dose greater than 50 g, preferably greater than 60 g, for example more than 70 g, even more preferably greater than 80 g, most preferably at least 90 g of the starch.

In a seventh aspect of the invention, there is provided the use of a starch in the preparation of a therapeutic foodstuff for the treatment of hypoglycaemia, wherein said starch is a waxy and/or hydrothermally treated starch.

Also provided by the invention is the use of starch in the preparation of a therapeutic foodstuff for the treatment or prevention of hypoglycaemic episode(s), for example night-time hypoglycaemic episode(s), wherein said starch is a waxy and/or hydrothermally treated starch.

Further provided by the invention is a therapeutic foodstuff comprising a starch, wherein said starch is a waxy and/or hydrothermally treated starch.

Therapeutic foodstuffs and food compositions of and for use in the invention may be provided in kit form. Accordingly, in a eighth aspect, the invention provides a therapeutic food kit, said food kit comprising:

a) a therapeutic food composition comprising starch, wherein said starch is a waxy and/or hydrothermally treated starch; and b) instructions for ingesting said therapeutic food composition.

The methods and therapeutic foodstuffs of and for use in the invention may be used to treat individuals with any disease associated with the presence or susceptibility to hypoglycaemia. Such diseases include, but are not limited to diabetes (Type I or Type II), glycogen storage disease, liver disease, for example, liver cirrhosis.

Moreover the methods and therapeutic foodstuffs of and for use in the invention are not limited to use with individuals having such disease. The demonstration by the present inventors that starches, which are waxy and/or hydrothermally treated, afford significantly prolonged glucose release in the GI tract compared to normal starches enables the use of such waxy and/or hydrothermally treated starches in therapeutic foodstuffs for sports nutrition, for example, to provide a sustained release food source during exercise, for example, prolonged exercise.

Accordingly, the invention further extends to the use of a starch in the preparation of sports nutrition foodstuff, wherein said starch is a waxy and/or hydrothermally treated starch.

Further provided by the invention is a sports nutrition foodstuff comprising a starch, wherein said starch is a waxy and/or hydrothermally treated starch.

Preferred features of each aspect of the invention are as for each of the other aspects mutatis mutandis.

DETAILED DESCRIPTION

As described above, the present inventors have discovered that existing treatments for conditions characterised by hypoglycaemic episodes may be improved and/or supplemented by the use of waxy starches as sources of α-glucan, thus enabling significant improvement to control over the rate of glucose formation and appearance in the blood mammals. Such starches significantly outperform the conventionally used 'corn starch' (native maize starch) in terms of duration of glucose release due to amylase hydrolysis in the small intestine.

Moreover, the inventors have shown that the glucose release profile may be further dramatically prolonged by modifications to the optimised starch e.g. by hydrothermal treatment for example, by heat moisture treatment. Indeed, hydrothermal treatment also provides considerable improvement in conventional non-waxy starches. Thus, the invention also extends to the methods of the first, second and third aspect of the invention, wherein the waxy starch is substituted by any hydrothermally treated starch, preferably heat moisture treated starch (whether waxy or non-waxy).

Starches

Starches are produced by plants as roughly spherical granules ranging in diameter from <5 to >50 μm. Depending on source they contain ~11-17% moisture, ~82-88% α-glucan, <~1.5% lipid and <~0.6% protein. The α-glucan comprises two types of molecules: amylose and amylopectin. The former is an essentially linear molecule comprising about 99% α-(1-4) and about 1% α-(1-6) bonds with a molecular weight of ~500,000. Amylopectin is much bigger than amylose with a molecular weight of a few million and is heavily branched with ~95% α-(1-4) and ~5% α-(1-6) bonds. The exterior chains of amylopectin associate together as double helices which themselves register together to form crystalline laminates. These crystalline laminates are interspersed with amorphous material comprising non-crystalline (branched regions) of amylopectin plus amylose. The amylose may form inclusion complexes in cereal starches with lipids causing the presence of two forms of the molecule: lipid complexed and lipid free.

In normal starches, amylopectin is the 'seat', of crystallinity. Waxy starches have a greater proportion of crystallinity due to the higher amylopectin content. High amylose starches contain both amylopectin and amylose generated crystalline material.

Starches containing <~20% amylose (80% amylopectin) are commonly referred to as 'waxy', ~20-40% are commonly referred to as 'normal' and ~>40% are commonly referred to as high amylose or amylo-starches. Normal maize and wheat starches are, for example, ~30% amylose.

The semi-crystalline native starch granules are insoluble and largely indigestible by man's digestive enzymes. The control of native starch digestion in man is not well understood although it does not provide a major nutritional focus as most starches are processed prior to cooking. Processing of starch incorporates cooking in water which disrupts the crystalline regions and 'gelatinises' the starch. Gelatinised starches are very digestible because of their amorphous nature by amylases and related enzymes in the small intestine of man. Native and resistant starches (see below), although in part digested in the small intestine, are fermented in the colon. Products of carbohydrate fermentation in the colon include short chain fatty acids (SCFAS) and gasses like carbon dioxide, hydrogen and methane.

Resistant starch takes a number of forms and simply resists hydrolysis by enzymes synthesised in the small intestine of man. This includes: small food particles entrapping starch; native starch; recrystallised (retrograded) starch and; chemically modified starch.

If starches are hydrolysed (typically chemically with acids or enzymatically with α-amylase and amyloglucosidase) smaller molecules called 'dextrins' are generated. Products may be as small as the smallest possible monosaccharide glucose or be slightly hydrolysed but still polymeric. Glucose syrups are made from starch hydrolysis and contain variable proportions of sugars and dextrins depending on the nature and extent of conversion. The extent of conversion is usually defined as dextrose equivalence (DE) which equates reducing power of the hydrolysate to that of pure dextrose (glucose).

Maltodextrins are DP20 or less, GRAS quality, tasteless and very soluble. They are easily digestible and are used in energy drinks because of their solubility and reportedly relatively slow digestibility compared to glucose (which is simply absorbed). The difference in rate of glucose appearance in the blood as a consequence of drinking glucose or maltodextrin solutions is relatively small (e.g. ~45 minutes) because of the extent of conversion of the maltodextrin.

In the present invention, any suitable semi-crystalline or crystalline starch may be used. In preferred embodiments, the starch of and for use in the invention is a waxy starch.

The starch may be a naturally produced starch or may be synthetically produced using any suitable method e.g. plant breeding or biotechnological methods (including transgenic technology etc.).

Preferred native starches are waxy with an average diameter of approximately 15-35 μm.

Hydrothermally Treated Starch

As discussed above and shown in the examples below, the inventors have found that particularly good results are obtained when using hydrothermally treated starch.

Two main methods are currently used for the hydrothermal treatment of starch: heat-moisture treatment (high temperature, low moisture) and annealing (high moisture, low temperature).

Heat Moisture Treated Starch (EMT Starch)

Heat and moisture treated starch is typically produced by exposing moist starch (e.g. 15-30% moisture) to temperatures of e.g. 95° C. to 130° for periods up to 30 hours (typically 16-24). These ranges do not exclude other heat-moisture profiles. For example, HMT starch for use in the invention may be produced by thermally treating starch in a sealed container under the following conditions: 20% moisture and 105° C. for 16 hours. The treated starch may then be cooled to room temperature, air-dried and then passed through 300 um sieve.

Such heat moisture treatment results in a number of significant property changes to starches. The extent of the effect varies with the type of starch but in general the effects are:
  increased gelatinisation temperature
  reduced water absorption and swelling power
  changed X-ray diffraction pattern
  increased enzyme susceptibility As described herein, although heat moisture treatment results in starches having increased susceptibility to enzymatic degradation, the inventors have surprisingly shown that when used in methods of the invention, heat moisture treated starches provide significantly greater prolongation of the time period over which serum glucose levels are maintained compared to the corresponding non heat moisture treated starches.

Annealing Treatment of Starch

In certain embodiments of the invention the starch of and for use in the invention is annealing treated starch. Any suitable annealing treated starch may be used.

Annealing is a process in which starch granules are treated for a relatively long time in excess amounts of water at a temperature slightly higher then room temperature. Typically, annealing of starch involves incubation of starch granules in water (>40% w/w), for a time period in the range 1 hour to 10 days at a temperature between the glass transition and the gelatinisation temperature. Preferred annealing conditions are less than 10° C. below the onset of gelatinisation temperature, in excess water for up to 7 days.

Treatment/Therapy

"Treatment" (which, unless the context demands otherwise, is used interchangeably with "therapy", includes any regime that can benefit a human or non-human animal. The treatment may be in respect of an existing condition or may be prophylactic (preventative treatment). Treatment may include curative, alleviation or prophylactic effects.

Food Compositions

The invention extends to a therapeutic food composition for the treatment of diseases characterised by hypoglycaemic episodes, wherein said composition comprises a semi-crystalline starch.

The therapeutic food compositions of and for use in the present invention may consist solely of said starches or preferably may comprise further additives. Such additives may contribute merely to the palatability of the composition, e.g. flavourings, or may contribute significant calorific value, for example, sugars with a more rapid release profile than the starches, or lipids. These compounds may be incorporated to slow gastric emptying and facilitate the effect (e.g. amino acids, lipids etc.).

The therapeutic food composition can take a variety of forms, for example as a food, a food supplement, a liquid, an emulsion or mixture thereof. Preferably, it is prepared as a ready to eat foodstuff, for example as a snackbar, a baked product, pasta or drink.

Alternatively, the therapeutic food composition may be administered as a pharmaceutical composition, which will generally comprise a suitable pharmaceutical excipient, diluent or carrier selected dependent on the intended route of administration.

Some suitable routes of administration include (but are not limited to) oral, rectal or parenteral (including subcutaneous, intramuscular, intravenous, intradermal) administration.

For intravenous injection the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

However, the composition is preferably for administration orally. Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

Examples of the techniques and protocols mentioned above and other techniques and protocols which may be used in accordance with the invention can be found in Remington's Pharmaceutical Sciences, 16th edition, Oslo, A. (ed), 1980.

Dose

The therapeutic food compositions of and for use in the invention are preferably administered to an individual in a "therapeutically effective amounts", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration.

The invention will now be described further in the following non-limiting examples. Reference is made to the accompanying drawings in which:

FIG. 1 shows schematically glucose and glycogen metabolism reactions.

FIG. 2 shows a comparison of the hydrolysis profile of native starches using the Karkalas et al (1992) procedure;

FIG. 3 shows blood glucose level after consumption of native starches;

FIG. 4 shows a comparison of the blood lactate level after consumption of native starches;

FIG. 5 shows a comparison of blood glucose after consumption of two native starches (wheat and waxy maize) with added pregelatinised (maize) starch;

FIG. 6 shows a comparison of the blood lactate level after consumption of two native starches (wheat and waxy maize) with added pregelatinised (maize) starch;

FIG. 7 shows a comparison of blood glucose after consumption of starch (native waxy maize and soluble) encapsulated with pectin and alginate.

FIG. 8 shows a comparison of blood lactate after consumption of starch (native waxy maize and soluble) encapsulated with pectin or alginate.

FIG. 9 shows a comparison of blood glucose after consumption of starch (native waxy maize, soluble) encapsulated with lipid.

FIG. 10 shows a comparison of blood glucose after consumption of heat-moisture treated waxy maize starch, waxy maize and normal maize starch.

FIG. 11 shows a comparison of blood lactate after consumption of heat-moisture treated waxy maize starch, waxy maize and normal maize starch.

FIG. 12 shows a comparison of digestibility of native and heat-moisture treated waxy maize starches.

FIG. 13 shows a comparison of digestibility of native and heat-moisture treated normal maize starches.

EXAMPLE 1

In Vitro Hydrolysis

Common native starches (barley, maize, potato, rice and wheat) were evaluated using the Karkalas et al (1992) (in vitro) method to identify their amylase hydrolysis profile and potential for slow release of energy in individuals. These data are presented in FIG. 2.

As can be seen from FIG. 2 that rice starch has a fast energy release profile initially followed by a much slower process. In contrast, potato and high amylose starches show great resistance towards amylase hydrolysis and are nearly untouched by the enzyme. Starches from normal maize, waxy maize and wheat show continuous slow release energy profile. These data provide the basis for an in vitro selection of the most appropriate starch for this purpose (as discussed later). Note that they do not define the rate or extent of hydrolysis in the actual gut but provide a means of ordering the rate of extent of hydrolysis based on the in vitro system.

EXAMPLE 2

Digestion of Native Starches

Under clinical supervision, individuals suffering from GSD were fed 60 g samples of native starches dispersed in semi-skimmed milk. The amount of blood glucose and lactate were monitored and are presented in FIGS. 3 and 4. Native potato starch was not consumed in view of is resistance to digestion (and cause of potential colonic disturbance accordingly).

These data show that waxy rice starch released glucose very quickly where the highest (too high) initial glucose peak (8.7 mmoll$^{-1}$) at 1 hour post ingestion was obtained. The blood glucose level then dropped to 3 mmoll$^{-1}$ within 4.5 hours (270 minutes). Normal rice showed a much lower initial glucose peak with a longer release profile corresponding to 3.2 mmoll$^{-1}$ within 5 hours (300 minutes) but less glucose released in the time course of the experiment compared to the waxy rice starch. High amylose starch too extensively restricted glucose release (although this could be moderated by physical/chemical/enzymatic or biotechnological modification). The normal maize starch ('corn starch') exhibited a low glucose peak 1 hour (6.6 mmoll$^{-1}$) after ingestion with an extended release of 2.9 mmoll$^{-1}$ after 300 minutes. The waxy maize starch surprisingly showed the optimal release profile with less than 7 mmoll$^{-1}$ blood glucose 1 hour post ingestion, a significant glucose release profile for up to 6 hours (330 minutes) which dropped to 2.9 mmoll$^{-1}$ at this point.

Lactate in the blood also reflected the starch consumed (FIG. 4). The high amylose maize starch provided the least lactate response (highest lactate) as it was little digested (FIG. 3). The greatest reduction in lactate was achieved by the waxy maize starch and in common with the previous data promotes its potential use for GSD and similar conditions requiring slow release of energy.

Based on these data, there is clearly a granule size and compositional effect that regulates native starch hydrolysis to glucose in the gut. There is a balance between choosing a starch for therapy based on the 1 hour glucose peak, duration of release and the amount (integrated area) of glucose release with time. A preferred starch for the purpose, therefore:
a) is highly crystalline (semi-crystalline) with waxy starches providing the most appropriate crystalline (amylopectin) matrices for this purpose.
b) has reasonably large granules without exceeding the digestive capacity. Rice starches (~5 µm diameter on average) are too small. Maize starch granules are preferred (~20-25 µm diameter on average).

It is recognised that the cereal starches contain lipid and that other starches may be more appropriate in terms of size and composition. However, in view of the lack of digestibility and potential dangers of eating large granules (which may cause colonic lesions) it is proposed that granules in excess of ~40 µm diameter are not consumed for this purpose.

EXAMPLE 3

Digestion of Native Starches in the Presence of a Pre-gelatinised Starch Thickener Under clinical supervision, individuals suffering from GSD were fed 60 g samples of two native starches (wheat or waxy maize), each sample containing 54 g of either starch and 6 g pregelatinised maize starch (National B37, National Starch & Chemical) dispersed in cold semi-skimmed milk. The amount of blood glucose and lactate were monitored and are presented in FIGS. 5 and 6.

These data show that even in the presence of amorphous (pre-gelatinised) starch the waxy maize starch resists digestion (FIG. 5) more than the wheat starch, which contains a bi-modal distribution of small (~10 µm average diameter) and large (~25 µm average diameter) granules but with similar composition (amylose, lipid, moisture and protein). This is reflected in a lower blood lactate (even though the patients started with a higher lactate content when presented with the waxy maize starch (as shown in FIG. 6). The importance of this work is that it shows that even if the waxy starch is mixed with other materials that have the capacity to provide a quicker glucose response it can still provide a slow release function.

EXAMPLE 4

Digestion of Native Starches in the Presence of Non-starch Polysaccharides

Native waxy maize starch (Amioca Powder T, National Starch) was encapsulated in soluble starch (Crystal Tex 626, National Starch) and pectin (LM-104AS-FS, CPKelco) or alginic acid (Manugel GMB, Manugel) according to Tester and Karkalas (1999). The final starch to non-starch polysaccharide (NSP) ratio was 5.7:1 or 19:1. The proportion of the soluble starch to native starch varied according to the proportion of native starch used for the two conditions but was the same for both non-starch polysaccharide conditions and simply serves as a comparison.

Under clinical supervision, individuals suffering from GSD were fed 70 g or 63 g (depends on the starch to NSP ratio) samples of NSP encapsulated starch dispersed in cold semi-skimmed milk. The amount of blood glucose and lactate were monitored and are presented in FIGS. 7 and 8.

These data show that, although the amount of starch modifies the extent of glucose release as expected, the alginate or pectin components do not stretch out the release profile much beyond 5 hours (300 minutes). Hence, the presence of a non-starch polysaccharide 'raft' or food matrix is not enough in itself to slow the rate of starch hydrolysis accordingly (whether native or soluble). The blood lactate response reflects the blood glucose where alginate appears to reduce lactate production more markedly than pectin (since it restricts hydrolysis more).

EXAMPLE 5

Digestion of Native Starches in the Presence of Lipid

Starch (Amioca Powder T, National Starch) with or without addition of soluble starch (Crystal Tex 626, National Starch) was encapsulated in lipid (Revel A, Loders Croklaan B. V.) as follows. The lipid was dissolved in the minimal amount of ethanol possible to dissolve the starch. The starch was then thoroughly mixed with the ethanol solution until homogeneous. The starch was laid on a tray and air at 35° C. was allowed to flow over the ethanol/lipid/starch system (in a fume cupboard) until the ethanol had all evaporated from the system. The final starch to lipid ratio was 9:1. When used, the proportion of soluble starch was 10% of the total starch fraction.

Under clinical supervision, individuals suffering from GSD were fed 66 g samples of lipid encapsulated starch dispersed in cold semi-skimmed milk. The amount of blood glucose was monitored and is presented in FIG. 9.

These data show that the lipid restricts the amount of starch digestion at all times (see previous figures for comparison). Overall, this approach is not appropriate for the control of glucose release (extent of hydrolysis) from the starch as the amount released over time and the actual duration is reduced.

EXAMPLE 6

Digestion of Hydrothermally Treated Starches

Starch (Amioca Powder T, National Starch) was thermally treated in a sealed container under the following conditions: 20% moisture and 105° C. for 16 hours. The treated starches were then cooled to room temperature, air-dried and then passed through 300 µm sieve.

Under clinical supervision, individuals suffering from GSD were fed 60 g or 90 g samples of heat-moisture treated starch dispersed in cold semi-skimmed milk. The amount of blood glucose and lactate were monitored and are presented in FIGS. 10 and 11.

These Data Show that:
(i) Heat moisture treated (HMT) waxy maize starch has a much reduced initial glucose response at 60 minutes than native waxy maize starch (FIG. 10).
(ii) Because of the reduced initial response more can be fed to be within acceptable levels of glucose increase at this time (where a preferred response is <8 mmol $l^{-1}$).
(iii) As a consequence of the above, greater amounts could be fed (90 g versus 60 g) leading to 7.5 hour (450 minutes) profile where the HMT starch can still maintain the blood glucose at ~2.5 mmol $l^{-1}$.
(iv) The glucose response provides an acceptable and desirable lactate response accordingly (FIG. 11).

Similar results were obtained when repeating the experiments on further patients (results not shown).

These data are reinforced by the in vitro assay as shown in FIG. 12. Here the HMT treatment can be shown to clearly restrict the hydrolysis of the waxy maize starch.

Hence, the combination of a waxy starch and its heat moisture treatment allows for the formation of a desirable slow release of glucose therapy. The waxy maize starch is potentially more crystalline than normal or high amylose starches in view of the high amylopectin content.

A particularly preferred type of starch for this purpose is: semi crystalline with, preferably, the highest proportion of crystallinity possible and with amylase accessibility enhanced by the heat moisture processing.

Moreover, in order to show that the advantages conferred by hydrothermal treatment is not limited to waxy starches, the digestibility of native and heat-moisture treated normal maize starch was tested using the same assay as in FIG. 12. The results are shown in FIG. 13. As shown in FIG. 13, hydrothermal treatment of normal maize starch (i.e. non-waxy starch) improves the hydrolysis profile of the starch. Thus, the results support the use of hydrothermally treated normal starch for slow release glucose therapy in the methods of the invention.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCES http<<colon>>//www<<dot>>accelerade<<dot>>com/accelerade-comparison-results<<dot>>asp
http<<colon>>//www<<dot>>agsd<<dot>>org<<dot>>uk/home/information<<dot>>asp
http<<colon>>//agsdus<<dot>>org/body_whatis1<<dot>>html
Berggren, A., Johansson, M. L., Larsson, K., Lindberg, A-M. and Wiklander, J. (2000) WO 00/70972 A1
Booth, G. P. (1999) U.S. Pat. No. 5,980,968
Brynolf, M., Ståhl, A. and Sandström, R (1999) U.S. Pat. No. 5,929,052
Burling, H., Ekelund, K. and Pettersson, H-E. (1989) WO 90/02494
Cooper, J. M., Acaster, M. A., Heath, C., Gleeson, M. and Botham, R. L. (2001) GB 2,356,788 A
Fisher, C., Lannelongue, M. L. H. and Hale, P. WO 94/06412
Gawen, P. (1981) GB 2,064,938 A
Gordeladze, J. (1997) WO 97/49304
Karkalas, J., Tester, R. F. and Morrison, W. R. (1992). Properties of damaged starch granules. I. Comparison of a new micromethod for the enzymic determination of damaged starch with the standard AACC and Farrand methods. *Journal of Cereal Science* 16, 237-251.
Kaufman, F. (2002) U.S. Pat. No. 6,339,076 B1
King, R. F. G. J. (1998) U.S. Pat. No. 5,780,094
Kurppa, L. J. (1998) WO 98/46091
Lapré, J. A. and McNabola, W. T. (1996) EP 0,749, 697 A1
Liao, G. (1995) CN 1,097,289
Paul, S. M. and Ashmead, D. H. (1993) U.S. Pat. No. 5,270,297
Paul, S. M. and Ashmead, D. H. (1994) U.S. Pat. No. 5,292,538
Pons Biescas, A., Tur Mari, J. A., Tauler Riera, P., Aguilo Pons, A., Cases, Porcel, N and Pina Florit, A. (2002) WO 03/001929 A1
Portman, R. (2002) US 2002/0197352 A1
Simone, C. B. (1995) U.S. Pat. No. 5,397,786
Strahl, R. C. (2000) U.S. Pat. No. 6,039,987.
Karkalas, J. and Tester, R. F. (1999) WO9953902.
Tauder, A. R., Costill, D. L., Mink, B. D. and Albrecht, J. L. (1986) EP 0,223,540 A2
Vinci, A., Cummings, K. R., Sweeney, T. F. and Lajoie, M. S. (1993) U.S. Pat. No. 5,244,681
Wilbert, G. J., Greene, H. L., Keating, K. R. and Lee, Y-H (1998) U.S. Pat. No. 5,776,887

The invention claimed is:
1. A method of treating hypoglycaemia in an individual in need of such treatment, said method including the step of administering to said patient a therapeutic food composition comprising a waxy maize starch which is a heat moisture- treated starch, wherein the heat moisture-treated starch is prepared by treating waxy maize starch under conditions of 15-30% moisture at a temperature of 95-130° C. for a period of 16-24 hours.

2. A method of treating an individual susceptible to hypoglycaemic episodes to prevent or decrease hypoglycaemic episode(s), said method including the step of administering to said individual a therapeutic food composition comprising a waxy maize starch which is a heat moisture-treated starch, wherein the heat moisture-treated starch is prepared by treating waxy maize starch under conditions of 15-30% moisture at a temperature of 95-130° C. for a period of 16-24 hours.

3. The method according to claim 2, wherein said individual has glycogen storage disease.

4. The method according to claim 2, wherein said individual has Type I or Type II diabetes.

5. The method according to claim 2, wherein said individual has liver disease.

6. The method according to claim 2, wherein the starch has an amylopectin content of at least 80%.

7. The method according to claim 2, wherein said therapeutic food composition comprises per unit dose sufficient starch to maintain blood glucose concentration of greater than 3.0 mmol $l^{-1}$ at 300 min post administration and wherein the starch does not cause a peak in blood glucose concentration of greater than 9.0 mmol $l^{-1}$.

8. The method according to claim 4, wherein said therapeutic food composition comprises per unit dose sufficient starch to main blood glucose concentration of greater than 2.25 mmol $l^{-1}$ at 450 min post administration.

9. The method according to claim 2, wherein said therapeutic food composition comprises per unit dose greater than 50 g of starch.

10. A therapeutic food kit, said food kit comprising:
   a) a therapeutic food composition comprising a waxy maize starch which is a heat moisture-treated starch, wherein the heat moisture-treated starch is prepared by treating waxy maize starch under conditions of 15-30% moisture at a temperature of 95-130° C. for a period of 16-24 hours; and
   b) instructions for treating hypoglycaemia or preventing or decreasing hypoglycaemic episode(s) by ingesting said therapeutic food composition.

11. A sports nutrition foodstuff comprising a heat moisture-treated waxy maize starch, wherein the heat moisture-treated starch is prepared by treating waxy maize starch under conditions of 15-30% moisture at a temperature of 95-130° C. for a period of 16-24 hours.

12. The method according to claim 2, wherein the heat moisture-treated starch is prepared by treating waxy maize starch under conditions of 20% moisture at a temperature of 105° C. for a period of 16 hours.

13. The method according to claim 2, wherein the heat moisture-treated starch shows increased susceptibility to enzymatic degradation compared to untreated waxy maize starch.

14. A method of treating hypoglycaemia in an individual in need, of such treatment, said method including the step of administering to said patient a therapeutic food composition comprising a waxy maize starch which is a heat moisture-treated starch, wherein said therapeutic food composition comprises per unit dose sufficient starch to maintain blood glucose concentration of greater than 3.0 mmol $l^{-1}$ at 300 min post administration and wherein the starch does not cause a peak in blood glucose concentration of greater than 9.0 mmol $l^{-1}$.

15. The method of claim 14, wherein the individual has a disorder selected from the group consisting of: glycogen storage disease; Type I diabetes; Type II diabetes; and liver disease.

16. A method of treating an individual susceptible to hypoglycaemic episodes to prevent or decrease hypoglycaemic episode(s), said method including the step of administering to said individual a therapeutic food composition comprising a waxy maize starch which is a heat moisture-treated starch, wherein said therapeutic food composition comprises per unit dose sufficient starch to maintain blood glucose concentration of greater than 3.0 mmol $l^{-1}$ at 300 min post administration and wherein the starch does not cause a peak in blood glucose concentration of greater than 9.0 mmol $l^{-1}$.

17. The method of claim 16, wherein the individual has a disorder selected from the group consisting of: glycogen storage disease; Type I diabetes; Type II diabetes; and liver disease.

18. A therapeutic food kit, said food kit comprising:
   a) a therapeutic food composition comprising a waxy maize starch which is a heat moisture-treated starch, wherein said therapeutic food composition comprises per unit dose sufficient starch to maintain blood glucose concentration of greater than 3.0 mmol $l^{-1}$ at 300 min post administration and wherein the starch does not cause a peak in blood glucose concentration of greater than 9.0 mmol $l^{-1}$; and
   b) instructions for treating hypoglycaemia or preventing or decreasing hypoglycaemic episode(s) by ingesting said therapeutic food composition.

* * * * *